United States Patent
Shirai et al.

Patent Number: 5,922,743
Date of Patent: Jul. 13, 1999

[54] PYRIDINE DERIVATIVE

[75] Inventors: Hirofusa Shirai, Chiisagata-Gun; Kenji Hanabusa, Ueda; Yuki Takahashi, Tokyo; Fumio Mizobe, Tokyo; Kazunori Hanada, Tokyo, all of Japan

[73] Assignee: Taisho Pharmaceutical Co., Ltd., Tokyo, Japan

[21] Appl. No.: 08/849,148

[22] PCT Filed: Nov. 27, 1995

[86] PCT No.: PCT/JP95/02399

§ 371 Date: Aug. 7, 1997

§ 102(e) Date: Aug. 7, 1997

[87] PCT Pub. No.: WO96/16942

PCT Pub. Date: Jun. 6, 1996

[30] Foreign Application Priority Data

Nov. 28, 1994 [JP] Japan ..................... 6-292608

[51] Int. Cl.⁶ ............... C07D 213/02; A61K 31/44
[52] U.S. Cl. .......................... 514/357; 546/334
[58] Field of Search ................... 546/334, 335; 514/357

[56] References Cited

FOREIGN PATENT DOCUMENTS

WO 94/14440  7/1994  WIPO.
WO 94/27604  12/1994  WIPO.

*Primary Examiner*—Zinna Northington Davis
*Attorney, Agent, or Firm*—Sughrue, Mion, Zinn, Macpeak & Seas, PLLC

[57] ABSTRACT

A pyridine derivative represented by the following formula:

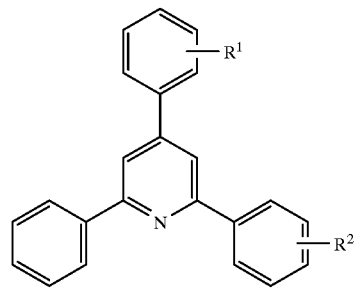

where $R^1$ and $R^2$ are as defined in the specification, or a salt thereof. These compounds directly or indirectly act on neuronal cells in vivo and are effective in the amelioration and curing of nerve disorders due to neuronal degeneration, such as, for example, traumatic symptoms and maladies, disorders induced by drugs such as alcohol and antineoplastic agents, inflammatory disorders, metabolic disorders observed in diabetes, and disorders due to idiopathic degeneration of peripheral nerves. These compounds are also effective for ameliorating and curing symptoms and maladies due to degeneration of central nerves, for example, Alzheimer's disease and cerebrovascular ischemia, Down's syndrome, Parkinson's disease, Huntington's chorea, diseases secondary to cerebral ischemia, cerebral infarction, intracerebral bleeding, head injuries, amnesia, and spinal neuropathy.

8 Claims, 1 Drawing Sheet

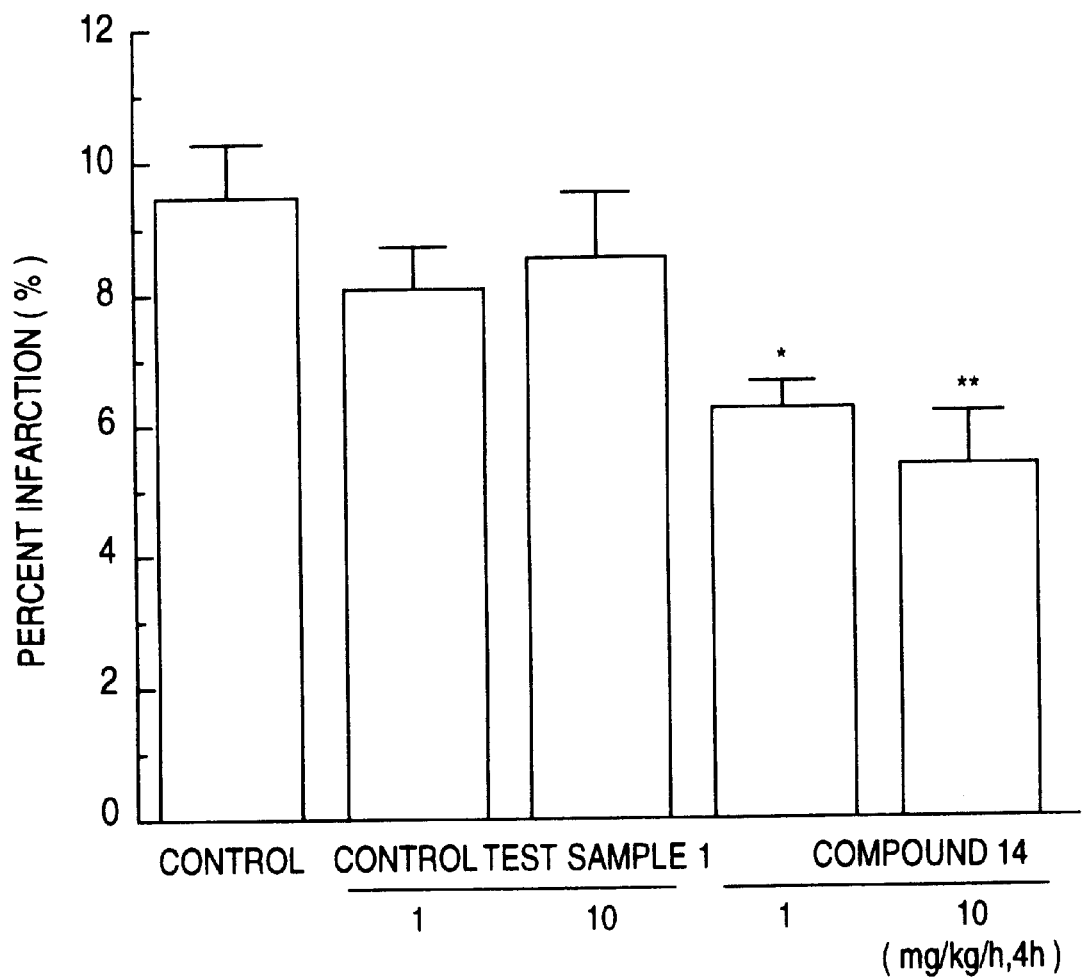

PYRIDINE DERIVATIVE

This application is a 371 of PCT/JP95/02399 filed Nov. 27, 1995.

TECHNICAL FIELD

The present invention relates to a pyridine derivative having an ability to act as a neurotrophic factor and a salt thereof.

BACKGROUND ART

It has been suggested that in Alzheimer's disease, which has recently been increasing in prevalence, degeneration and dysfunction of cholinergic neurons are intimately related to memory disorder and lowering of intellectual activity [Witehorse et al: Science, 215, 1237 (1982)].

It has been reported that NGF can suppress the degeneration and dysfunction of centrally cholinergic neurons of the central nervous system due to fiber breakage [Korsing et al: Neuroscience Lett., 66, 175 (1986)] and also can ameliorate maze learning disorder of aged rats and suppress atrophy of cholinergic neurons [T. Shigeno et al: Igakuno Ayumi (Advances in drug), 145, 579 (1986)]. These show that NGF can serve as a drug for curing Alzheimers disease. Furthermore, it has been confirmed that NGF can prevent death of hippocampal neuronal cells after cerebral ischemia in gerbils, and it can be presumed that NGF is a useful drug for curing secondary disorder of cerebral ischemia.

On the other hand, it has been clarified that NGF functions to promote recovery of peripheral neuropathy and is a useful drug for curing the peripheral neuropathy. In addition to NGF, many biomolecules having the ability to maintain the survival and functioning of neuronal cells or showing an ability to remedy degeneration have been found, and they are now called neurotrophic factors. Thus, it can be presumed that these neurotrophic factors are useful drugs for curing central neuronal degeneration and peripheral neuropathy. All the biomolecules called neurotrophic factors including NGF are proteins. In using proteins as drugs for curing central nerve disorders, it can be presumed from their properties that intracerebroventricular administration must be carried out. Thus, there are still many practical problems.

Accordingly, a drug comprising a low molecular weight compound having the ability to act as a neurotrophic factor capable of more simple administration has been desired. Thus, an object of the present invention is to provide a novel compound having the ability to act as a neurotrophic factor.

DISCLOSURE OF THE INVENTION

As a result of extensive studies on a large number of compounds to attain the above-mentioned object, the present inventors have found that some pyridine derivatives have the ability to act as a neurotrophic factor and have established the present invention.

That is, the present invention provides a pyridine derivative represented by the following formula:

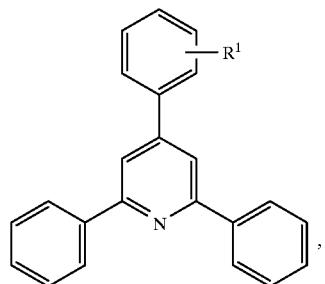
(I)

where $R^1$ shows the ability group represented by any one of the following formulae (II)-1 to (II)-6:

 (II)-1

 (II)-2

 (II)-3

 (II)-4

 (II)-5

 (II)-6 or a salt thereof, and a pyridine derivative represented by the following formula:

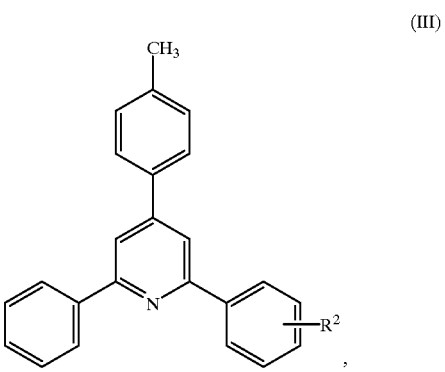
(III)

where $R^2$ shows an amino group or the ability group represented by any one of the following formulae (IV)-1 to (IV)-5:

 (IV)-1

 (IV)-2

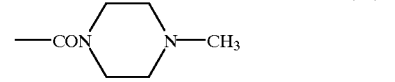 (IV)-3

-continued

  (IV)-4

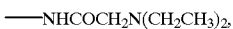  (IV)-5 or a salt thereof.

In the present invention, a salt of pyridine derivative means a pharmacologically acceptable salt, and includes, for example, salts with a mineral acid such as hydrochloric acid, sulfuric acid, phosphoric acids nitric acid, etc., and salts with an organic acid such as citric acid, succinic acid, tartaric acid, methanesulfonic acid, etc.

The present compound can be prepared, for example, according to the following procedure:

First, a compound represented by the following formula:

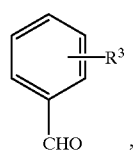  (V)

where $R^3$ is a methyl group, a carboxyl group or an acetamide group, and a compound represented by the following formula:

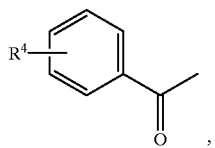  (VI)

where $R^4$ is a hydrogen atom, a carboxyl group or an acetamide group, are subjected to condensation in the presence of an alkali, whereby a compound represented by the following formula:

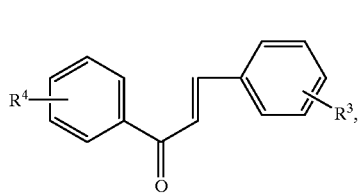  (VII)

where $R^3$ and $R^4$ have the same meanings as defined above, can be obtained.

An alkali for use in the condensation reaction includes, for example, potassium hydroxide, sodium hydroxide, sodium methoxide, potassium t-butoxide, potassium carbonate, sodium carbonate, sodium hydrogen carbonate, potassium hydrogen carbonate, etc. As a reaction solvent, methanol, ethanol, n-propanol, isopropanol, t-butanol, etc. can be used alone or in a mixture with water. Reaction temperature can be properly selected from a range of 0° C. to the boiling point of the solvent used.

Then, the compound of formula (VII) and a compound represented by the following formula:

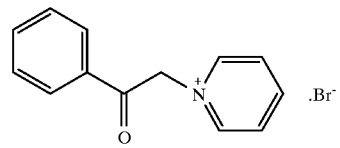  (VIII)

are subjected to reaction in the presence of ammonium acetate, whereby a compound represented by the following formula:

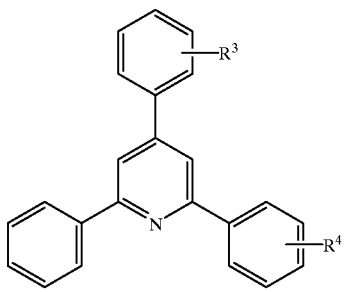  (IX)

where $R^3$ and $R^4$ have the same meanings as defined above, can be obtained. Ammonium acetate can be used in a 1 to 10-fold molar amount of the compound of formula (VII), and as a reaction solvent, methanol, ethanol, n-propanol, isopropanol, t-butanol, acetic acid, etc. can be used. Reaction temperature can be properly selected from a range of room temperature to the boiling point of the solvent used.

1) Compounds of formula (I), whose $R^1$ is a functional group represented by any one of formulae (II)-1 to (II)-4, and compounds of formula (III), whose $R^2$ is the ability group represented by any one of formulae (IV)-1 to (IV)-3, can be prepared in the following manner:

That is, pyridine derivatives obtained according to the above-mentioned procedure and represented by the following formula:

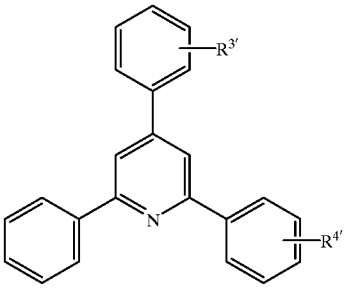  (X)

where $R^{4'}$ is a hydrogen atom when $R^{3'}$ is a carboxyl group and $R^{4'}$ is a carboxyl group when $R^{3'}$ is a methyl group, are subjected to the action with a halogenating agent to make an acid halide, followed by reaction with a corresponding amine or alcohol, whereby the desired compounds of the present invention can be obtained. As a halogenating agent, for example, thionyl chloride, phosphorus pentachloride, phosphorus oxychloride, oxalyl chloride, thionyl bromide, phosphorus tribromide, etc. can be used.

2) Compounds of formula (I), whose $R^1$ is a functional group represented by any one of formulae (II)-5 and (II)-6, and compounds of formula (III), whose $R^2$ is an amino group or the ability group represented by any one of formulae (IV)-4 and (IV)-5, can be prepared in the following manner:

That is, the acetamide groups of pyridine derivatives obtained according to the above-mentioned procedure and represented by the following formula:

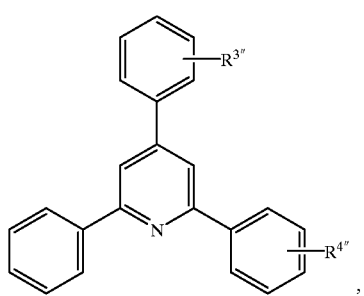

(XI)

where $R^{4''}$ is a hydrogen atom when $R^{3''}$ is an acetamide group and $R^{4''}$ is an acetamide group when $R^{3''}$ is a methyl group, are hydrolyzed in the presence of an acid or an alkali to obtain compounds having an amino group, followed by reaction with chloroacetyl chloride to amidize the compounds and then by reaction with a corresponding amine whereby the desired compounds of the present invention can be obtained.

BRIEF DESCRIPTION OF THE DRAWING

FIG. 1 shows effects of compound 14 and control sample 1 on cerebral infarction induced by middle cerebral artery occlusion in rats.

BEST MODES FOR CARRYING OUT THE INVENTION

The present pyridine derivatives can be orally or parenterally administered. Dosage depends on the type of medicine, but an appropriate dosage is 1 to 1,000 mg/adult/day.

In case of oral administration, the drug is mixed with a vehicle, a disintegrator, a binder, a lubricant, an antioxidant, a coating agent, a coloring agent, a corrigent, a surfactant, a plasticizer, etc. and administered as granules, powders, capsules or tablets. In case of parenteral administration, the drug can be administered as an injection, a drip infusion solution, or a suppository. In the foregoing medicinal preparation, any ordinary procedure for medicinal preparation can be used.

EXAMPLES

The present invention will be described in detail below, referring to Examples and Reference Examples.

In Tables 1 and 2, structural formulae of pyridine derivatives according to Examples of the present invention are shown.

TABLE 1

Structural formula

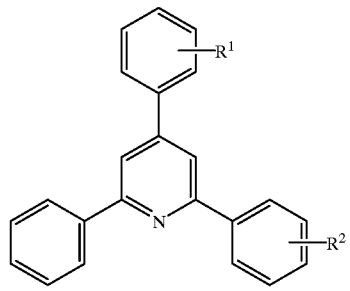

| Compound | $R^1$ | $R^2$ | Salt |
|---|---|---|---|
| 1 | 3-CONHCH$_2$CH$_2$N(CH$_3$)$_2$ | H | |
| 2 | 3-CONHCH$_2$CH$_2$N(CH$_3$)$_2$ | H | 2HCl |
| 3 | 3-CONHCH$_2$CH$_2$CH$_2$N(CH$_3$)$_2$ | H | |
| 4 | 3-CONHCH$_2$CH$_2$CH$_2$N(CH$_3$)$_2$ | H | 2HCl |
| 5 | 4-CONHCH$_2$CH$_2$N(CH$_3$)$_2$ | H | |
| 6 | 4-CONHCH$_2$CH$_2$N(CH$_3$)$_2$ | H | 2HCl |
| 7 | 4-CONHCH$_2$CH$_2$CH$_2$N(CH$_3$)$_2$ | H | |
| 8 | 4-CONHCH$_2$CH$_2$CH$_2$N(CH$_3$)$_2$ | H | 2HCl |
| 9 | 4-COOCH$_2$CH$_2$N(CH$_3$)$_2$ | H | |
| 10 | 4-COOCH$_2$CH$_2$N(CH$_3$)$_2$ | H | 2HCl |
| 11 | 4-COOCH$_2$CH$_2$N(CH$_2$CH$_3$)$_2$ | H | |
| 12 | 4-COOCH$_2$CH$_2$N(CH$_2$CH$_3$)$_2$ | H | 2HCl |
| 13 | 4-NHCOCH$_2$N(CH$_3$)$_2$ | H | |
| 14 | 4-NHCOCH$_2$N(CH$_3$)$_2$ | H | 2HCl |
| 15 | 4-NHCOCH$_2$N(CH$_2$CH$_3$)$_2$ | H | |

TABLE 2

Structural formula

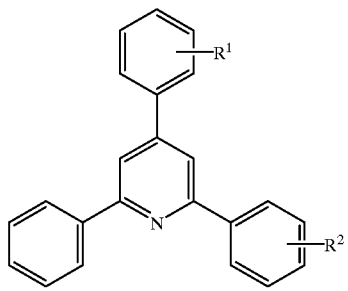

| Compound | R¹ | R² | Salt |
|---|---|---|---|
| 16 | 4-NHCOCH$_2$N(CH$_2$CH$_3$)$_2$ | H | 2HCl |
| 17 | 4-CH$_3$ | 4-CONHCH$_2$CH$_2$N(CH$_3$)$_2$ | |
| 18 | 4-CH$_3$ | 4-CONHCH$_2$CH$_2$N(CH$_3$)$_2$ | 2HCl |
| 19 | 4-CH$_3$ | 4-CON⟨piperazine⟩N—CH$_3$ | |
| 20 | 4-CH$_3$ | 4-CON⟨piperazine⟩N—CH$_3$ | 2HCl |
| 21 | 4-CH$_3$ | 4-COOCH$_2$CH$_2$N(CH$_3$)$_2$ | |
| 22 | 4-CH$_3$ | 4-COOCH$_2$CH$_2$N(CH$_3$)$_2$ | HCl |
| 23 | 4-CH$_3$ | 3-NH$_2$ | |
| 24 | 4-CH$_3$ | 3-NHCOCH$_2$N(CH$_3$)$_2$ | |
| 25 | 4-CH$_3$ | 3-NHCOCH$_2$N(CH$_3$)$_2$ | 2HCl |
| 26 | 4-CH$_3$ | 3-NHCOCH$_2$N(CH$_2$CH$_3$)$_2$ | |
| 27 | 4-CH$_3$ | 3-NHCOCH$_2$N(CH$_2$CH$_3$)$_2$ | 2HCl |
| 28 | 4-CH$_3$ | 4-NH$_2$ | |
| 29 | 4-CH$_3$ | 4-NHCOCH$_2$N(CH$_3$)$_2$ | |
| 30 | 4-CH$_3$ | 4-NHCOCH$_2$N(CH$_3$)$_2$ | 2HCl |

Reference Example 1

(E)-3-(4-carboxyphenyl)-1-phenyl-2-propen-1-one

A solution containing 4.10 g of potassium hydroxide dissolved in 50 ml of water was dropwise added to a mixture consisting of 8.00 g of acetophenone, 10.00 g of terephthalaldehydic acid and 40 ml of ethanol at 0° C. with stirring, and stirring was continued at 0° C. to 10° C. for further 6 hours.

After the completion of reaction, 3N hydrochloric acid was added thereto to acidify the reaction mixture, and the resulting product was recovered therefrom by filtration. By recrystallization from ethanol, 11.93 g of the captioned compound was obtained.

The following compounds were obtained substantially in the same manner as above, using acetophenone and corresponding aldehydes.

(E)-3-(3-carboxyphenyl)-1-phenyl-2-propen1-one
(E)-1-(3-carboxyphenyl)-3-(4-methylphenyl)-2-propen-1-one
(E)-1-(4-carboxyphenyl)-3-(4-methylphenyl)-2-propen-1-one
(E)-3-(4-acetamidophenyl)-1-phenyl-2-propen-1-one
(E)-1-(3-acetamidophenyl)-3-(4-methylphenyl)-2-propen-1-one
(E)-1-(4-acetamidophenyl)-3-(4-methylphenyl)-2-propen-1-one Reference Example 2

4-(4-carboxyphenyl)-2,6-diphenylpyridine 40 ml of methanol was added to 5.00 g of (E)-3-(4-carboxyphenyl)-1-phenyl-2-propen-1-one obtained in Reference Example 1, 5.51 g of phenacylpyridinium bromide and 7.63 g of ammonium acetate and the mixture was refluxed for 12 hours. After cooling, the product was recovered therefrom by filtration, and 3.90 g of the captioned compound was obtained by recrystallization from ethanol.

The following compounds were obtained substantially in the same manner as above, using corresponding α,β-unsaturated ketones in place of (E)-3-(4-carboxyphenyl)-1-phenyl-2-propen-1-one.

4-(3-carboxyphenyl)-2,6-diphenylpyridine
2-(3-carboxyphenyl)-4-(4-methylphenyl)-6-phenylpyridine
2-(4-carboxyphenyl)-4-(4-methylphenyl)-6-phenylpyridine
4-(4-acetamidophenyl)-2,6-diphenylpyridine
2-(3-acetamidophenyl)-4-(4-methylphenyl)-6-phenylpyridine
2-(4-acetamidophenyl)-4-(4-methylphenyl)-6-phenylpyridine Reference Example 3
4-(4-aminophenyl)-2,6-diphenylpyridine 1.50 g of sodium hydroxide, 100 ml of ethanol and 10 ml of water were added to 1.50 g of 4-(4-acetamidophenyl)-2, 6-diphenylpyridine obtained on the basis of Reference Example 2 as a reference, and the mixture was refluxed for 46 hours. After cooling, 100 ml of water was added thereto, and the resulting product was recovered therefrom by filtration. By recrystallization from ethanol, 1.17 g of the captioned compound was obtained.

Example 1
N-[2-(dimethylamino)ethyl]-4-(2,6-diphenyl-4-pyridyl) benzamide (Compound 5)

1.00 g of 4-(4-carboxyphenyl)-2,6diphenylpyridine obtained in Reference Example 2 was dissolved in 50 ml of toluene, and 0.62 ml of thionyl chloride was added thereto. The mixture was refluxed for 2 hours. Toluene and excess thionyl chloride were evaporated under reduced pressure, whereby an acid chloride was obtained. Then, 50 ml of chloroform was added to the acid chloride, and a solution containing 0.34 ml of N,N-dimethylethylenediamine in 10 ml of chloroform was dropwise, added thereto with stirring while ice cooling. Stirring was continued at room temperature for further 30 minutes.

The reaction solution was washed successively with an aqueous sodium bicarbonate saturated solution, water and an aqueous sodium chloride saturated solution in this order and dried over anhydrous sodium sulfate. The solvent was evaporated under reduced pressure, and the residues were recrystallized from ethyl acetatehexane, whereby 0.65 g of the captioned compound was obtained.

m.p.: 143.5–144.0° C.

The following compounds were obtained substantially in the same manner as above, using corresponding pyridine derivatives having a carboxyl group and corresponding amines in place of 4-(4-carboxyphenyl)-2,6-diphenylpyridine and N,N-dimethylethylenediamine.
N-[2-(dimethylamino)ethyl]-3-(2,6-diphenyl-4-pyridyl) benzamide (Compound 1)
    m.p.: 162.5–164.5°
N-[3-(dimethylamino)propyl]-3-(2,6-diphenyl-4-pyridyl) benzamide (Compound 3)
    m.p.: 143.0–145.0° C.
N-[3-(dimethylamino)propyl]-4-(2,6-diphenyl-4-pyridyl) benzamide (Compound 7)
    m.p.: 100.0–102.0° C.
N-[2-(dimethylamino)ethyl]-4-[4-(4-methylphenyl)-6-phenyl-2-pyridyl] benzamide (Compound 17)
    m.p.: 149.7–150.6° C.
4-(4-methylphenyl)-2-[4-(4-methylpiperazine-1-yl-carbonyl)phenyl]-6-phenylpyridine (Compound 19)
    m.p.: 133.0–134.5° C.

Example 2
2-dimethylamino)ethyl 4-(2,6-diphenyl-4-pyridyl) benzoate (Compound 9)

0.60 g of 4-(4-carboxyphenyl)-2,6-diphenylpyridine obtained in Reference Example 2 was dissolved in 50 ml of toluene, and 0.37 ml of thionyl chloride was added thereto. The mixture was refluxed for 5 hours. Toluene and excess thionyl chloride were evaporated under reduced pressures whereby an acid chloride was obtained. 20 ml of chloroform was added to the acid chloride. A solution containing 0.19 ml of N,N-dimethylethanolamine in 5 ml of chloroform was dropwise added thereto with stirring while ice cooling. Stirring was continued at room temperature for further 17 hours The reaction solution was washed successively with an aqueous sodium bicarbonate saturated solution, water and an aqueous sodium chloride saturated solution in this order and dried over anhydrous sodium sulfate. The solvent was evaporated under reduced pressure, and the residues were purified by column chromatography (developing solvent:dichloromethane:methanol=20:1), whereby 0.41 g of the captioned compound was obtained.

m.p.: 104.7–105.7° C.

The following compounds were obtained substantially in the same manner as above, using corresponding pyridine derivatives having a carboxyl group and corresponding N,N-dialkylethanolamines in place of 4-(4-carboxyphenyl)-2,6-diphenylpyridine and N,N-dimethylethanolamine.
2-(diethylamino)ethyl 4-(2,6-diphenyl-4-pyridyl) benzoate (Compound 11)
    m.p.: 207.0–209.0° C. (decomposed)
2-(dimethylamino)ethyl 4-[4-(4-methylphenyl)-6-phenyl-2-pyridyl] benzoate (Compound 21)
    m.p.: 117.2–118.8° C.

Example 3
2-(4-aminophenyl)-4-(4-methylphenyl)-6-phenylpyridine (Compound 28)

70 ml of 3N hydrochloric acid was added to 3.05 g of 2-(4-acetamidophenyl)-4-(4-methylphenyl)-6-phenylpyridine obtained on the basis of Reference Example 2 as a reference, and the mixture was refluxed for 2 hours. After cooling, an aqueous 10% sodium hydroxide solution was added thereto to make the mixture alkaline, and then the resulting product was extracted with ethyl acetate. The extract was washed successively with water and an aqueous sodium chloride saturated solution in this order and dried over anhydrous sodium sulfate. The solvent was evaporated under reduced pressure, and the residue were recrystallized from ethyl acetate-n-hexane whereby 2.26 g of the captioned compound was obtained.

m.p.: 137.0–139.0° C.

The following compound was obtained substantially in the same manner as above, using a corresponding pyridine derivative having an acetamide group in place of 2-(4-acetamidophenyl)-4-(4-methylphenyl)-6-phenylpyridine.
2-(3-aminophenyl)-4-(4-methylphenyl)-6-phenylpyridine (Compound 23)
    m.p.: 132.5–134.0° C.

Example 4
2-dimethylamino-N-[4-(2,6-diphenyl-4-pyridyl)phenyl] acetamide (Compound 13)

(1) 50 ml of chloroform was added to 1.30 g of 4-(4-aminophenyl)-2,6-diphenylpyridine obtained in Reference Example 3, and a solution containing 0.32 ml of chloroacetyl chloride in 10 ml of chloroform was dropwise added thereto with stirring while ice cooling. Stirring was continued at room temperature for further one hour. The reaction solution was washed successively with an aqueous sodium bicarbonate saturated solutions, water and an aqueous sodium chloride saturated solution in this order and dried over anhydrous sodium sulfate. The solvent was evaporated under reduced pressure, and the residues were recrystallized from ethyl acetate-n-hexane, whereby 1.33 g of 2-chloro-N-[4-(2,6-diphenyl-4-pyridyl)phenyl]acetamide was obtained.

m.p.: 214.5–215.2° C.

(2) 0.87 g of 2-chloro-N-[4-(2,6-diphenyl-4-pyridyl) phenyl] acetamide was dissolved in 50 ml of methanol, and 2.29 ml of an aqueous 50% dimethylamine solution was added thereto. The mixture was refluxed for 7 hours. The solvent was evaporated under reduced pressure, and an aqueous sodium bicarbonate saturated solution was added to the residues, followed by extraction with ethyl acetate. The extract was washed successively with water and an aqueous sodium chloride saturated solution in this order, and dried over anhydrous sodium sulfate. The solvent was evaporated under reduced pressure, and the residues were recrystallized from ethyl acetate-n-hexane whereby 0.81 g of the captioned compound was obtained.

m.p.: 173.5–174.9° C.

The following compounds were obtained substantially in the same manner as above, using corresponding pyridine derivatives having an amino group and corresponding amines in place of 4-(4-aminophenyl)-2,6-diphenylpyridine and dimethylamine.

2-dimethylamino-N-[[3-[4-(4-methylphenyl)-6-phenyl-2-pyridyl]phenyl]acetamide (Compound 24)

m.p.: 118.0–120.0° C.

2-dimethylamino-N-[[4-[4-(4-methylphenyl)-6-phenyl-2-pyridyl]phenyl]acetamide (Compound 29)

m.p.: 130.8–132.8° C.

2-diethylamino-N-[4-(2,6-diphenyl-4-pyridyl)phenyl] acetamide (Compound 15)

$^1$H NMR (CDCl$_3$) δ (ppm): 1.13 (6H, t, J=7.1 Hz)g 2.69 (4H, quart., J=7.2 Hz), 3.20 (2H, s), 7.41–7.57 (6H, m), 7.76 (4H, s), 7.88 (2H, s), 8.17–8.23 (4H, m), 9.57 (1H, br. s). MS(EI) 435 (M$^+$)

2-diethylamino-N-[[3-[4-(4-methylphenyl)-6-phenyl-2-pyridyl]phenyl]acetamide (Compound 26)

$^1$H NMR (CDCl$_3$) δ (ppm): 1.13 (6H, t, J=7.1 Hz), 2.45 (3H, s), 2.69 (4H, quart., J=7.2 Hz), 3.20 (2H, s), 7.32–8.30 (15H, m), 9.53 (1H, br. s) MS(CI) 450 (M+1)

Example 5

N-[2-(dimethylamino)ethyl]-4-(2,6-diphenyl-4-pyridyl) benzamide dihydrochloride (Compound 6)

1.50 ml of a 4N hydrochloric acid-ethyl acetate solution was added to a mixture consisting of 0.50 g of N-[2-(dimethylamino)ethyl]-4-(2,6-diphenyl-4-pyridyl) benzamide obtained in Example 1 and 30 ml of ethyl acetate with stirring. Stirring was continued at room temperature for 10 minutes. By recovering the resulting crystals therefrom by filtration, 0.46 g of the captioned compound was obtained.

m.p.: 250.0–251.5° C. (decomposed)

The following compounds were obtained substantially in the same manner as above, using corresponding pyridine derivatives in place of N-[2-(dimethylamino)ethyl]-4-(2,6-diphenyl-4-pyridyl)benzamide.

N-[2-(dimethylamino)ethyl]-3-(2,6-diphenyl-4-pyridyl) benzamide dihydrochloride (Compound 2) m.p.: 135.0–137.0° C.

N-[3-dimethylamino)propyl]-3-(2,6-diphenyl-4-pyridyl) benzamide dihydrochloride (Compound 4)

m.p.: 119.0–121.0° C.

N-[3-(dimethylamino)propyl]-4-(2,6-diphenyl-4-pyridyl) benzamide dihydrochloride (Compound 8)

m.p.: 242.0–244.0° C.

2-(dimethylamino)ethyl 4-(2, 6-diphenyl-4-pyridyl) benzoate dihydrochloride (Compound 10)

m.p.: 203.0–205.0° C.

2-(diethylamino)ethyl 4-(2,6-diphenyl-4-pyridyl)benzoate dihydrochloride (Compound 12)

m.p.: 204.0–206.0° C.

2-dimethylamino-N-[4-(2,6-diphenyl-4-pyridyl)phenyl] acetamide dihydrochloride (Compound 14)

m.p.: 232.0–234.0° C.

MS(EI); 407 (M$^+$-2HCl)

$^1$HNMR (DMSO-d6) δ (ppm): 2.91 (6H, d, J=3.5 Hz), 4.25 (2H, d, J=3.9 Hz), 7.45–7.62 (6H, m), 7.86 (2H, d, J=8.8 Hz), 8.12 (2H, d, J=8.6 Hz), 8.21 (2H, s); 8.33 (4H, dd, J=8.0, 1.5 Hz), 10.13 (1H, brs), 11.25 (1H, s).

2-diethylamino-N-[4-(2,6-diphenyl-4-pyridyl)phenyl] acetamide dihydrochloride (Compound 16)

m.p.: 236.0–238.0° C.

N-[2-(dimethylamino)ethyl]-4-[4-(4-methyl-phenyl)-6-phenyl-2-pyridyl]benzamide dihydrochloride (Compound 18)

m.p.: 221.0–223.0° C.

4-(4-methylphenyl)-2-[4-(4-methylpiperazin-1-ylcarbonyl) phenyl]-6-phenylpyridine dihydrochloride (Compound 20)

m.p.: 167.0–169.0° C.

2-(dimethylamino)ethyl 4-[4-(4-methylphenyl)-6-phenyl-2-pyridyl]benzoate hydrochloride (Compound 22)

m.p.: 106.0–108.0° C.

2-dimethylamino-N-[[3-[4-(4-methylphenyl)-6-phenyl-2-pyridyl]phenyl]acetamide dihydrochloride (Compound 25)

m.p.: 143.0–145.0° C.

2-diethylamino-N-[[3-[4-(4-methylphenyl)-6-phenyl-2-pyridyl]phenyl]acetamide dihydrochloride (Compound 27)

m.p.: 123.0–125.0° C.

2-dimethylamino-N-[[4-[4-(4-methylphenyl)-6-phenyl-2-pyridyl]phenyl]acetamide dihydrochloride (Compound 30)

m.p.: 257.0–259.0° C.

Industrial Applicability

NGF has a role in the maintenance of survival and functioning of some kinds of neuronal cells and has a function of remedying and protecting against degeneration. Pyridine derivatives of the present invention show an activity of prolonging the survival of cultured cortical neurons. Thus, the pyridine derivatives of the present invention directly or indirectly act on neuronal cells in vivo and are expected to be effective in ameliorating and curing nerve disorders due to neuronal degeneration. They can be used as drugs for ameliorating and curing, for example, traumatic symptoms and maladies, disorders induced by drugs such as alcohol, antineoplastic agents, etc., inflammatory disorders, metabolic disorders as observed in diabetes, etc., and furthermore disorders due to idiopathic degeneration of peripheral nerves.

Furthermore, they can be used as drugs for ameliorating and curing symptoms and maladies due to degeneration of central nerves, for example, Alzheimer's disease and cerebrovascular ischemia, Down's syndrome, Parkinson's disease, Huntington chorea, diseases secondary to cerebral ischemia, cerebral infarction, intracerebral bleeding, head injuries, etc, amnesia, spinal neuropathy, etc.

Test Exaple 1

[Test on Function to Act as a Neurotrophic Factor]

Function to act as a neurotrophic factor was evaluated according to the following procedure.

(Test Samples)

Individual compounds shown in Tables 1 and 2 were dissolved in DMSO, respectively, to make a concentrations of 2 mg/ml to 10 mg/ml.

(Test Cells)

The primary culture of cerebral cortical neuron from 18-day-old rat embryo.

(Test Procedure)

Test cells were plated at a density of 3.2×10$^6$ cells/ml in a 1:1 mixture of Dullbecco's modified Eagle's medium (available from Gibco Co.) and Ham's F12 medium containing 20% fetal bovine serum on a 24-well dishes coated with polyethyleneimine (with an area of 2 cm$^2$ per culture well; available from Corning) at 0.5 ml/well and cultured at 37° C. with 5% CO$_2$. After 24 hours of incubation, the culture medium was changed to a serum-free DF medium each containing one of test samples at a given concentration, 5 µg/ml of transferrin, 5 µg/ml of insulin and 20 p mole/ml of progesteron at 0.5 ml/well. The present compounds were added thereto in solution in DMSO with final concentrations as given in the following Table 3. For control, a medium containing only DMSO was used. At this stage, a pair of the same plates were made ready for each test sample. After 72 hours of incubation, a low oxygen load culturing was carried out for one of the plates in a $N_2$—$O_2$—$CO_2$ incubator (Model BNP-100, available from Tabai Co.) for 4 hours by lowering the oxygen concentration to 1% of the set minimum concentration. For another plate, culturing was continued without any load, while keeping 5% $CO_2$ and 95% air. Culturing was carried out for further 48 hours, and then the number of living cells was measured as follows: The medium was removed, and a fluorescien diacetate (FDA) reagent was added to each well. After washing with a phosphoric acid buffer (pH 7.4), fluorescence intensity (Ex 485/Em 530) was measured (Model Cyto Flour™ 2300, available from Millipore Co.).

Activities of neurotrophic factors of the present compounds were given in ratio to the fluorescence intensity of control (DMSO-admixed) as 1.0.
(Results)
Results are shown in Table 3.

TABLE 3

| Test sample | Concentration | Activity of neurotrophic factor | |
|---|---|---|---|
| | | Low oxygen | No treatment |
| Control (DMSO) | | 1.0 | 1.0 |
| Compound 2 | 2 µg/ml | 3.3 | 3.5 |
| | 10 µg/ml | 1.2 | 1.2 |
| Compound 4 | 2 µg/ml | 1.7 | 2.1 |
| Compound 6 | 2 µg/ml | 3.3 | 3.5 |
| | 10 µg/ml | 1.1 | 1.2 |
| Compound 8 | 2 µg/ml | 2.7 | 2.4 |
| | 10 µg/ml | 1.2 | 1.2 |
| Compound 10 | 2 µg/ml | 3.6 | 4.6 |
| Compound 12 | 2 µg/ml | 3.2 | 3.3 |
| Compound 14 | 2 µg/ml | 4.3 | 4.0 |
| Compound 16 | 2 µg/ml | 3.7 | 3.5 |
| Compound 18 | 2 µg/ml | 3.9 | 3.9 |
| Compound 20 | 2 µg/ml | 3.9 | 4.3 |
| Compound 22 | 2 µg/ml | 4.2 | 4.2 |
| Compound 23 | 2 µg/ml | 8.1 | 8.0 |
| | 10 µg/ml | 9.7 | 9.4 |
| Compound 25 | 2 µg/ml | 6.0 | 5.5 |
| Compound 27 | 2 µg/ml | 3.2 | 3.4 |
| | 10 µg/ml | 2.8 | 2.5 |
| Compound 28 | 2 µg/ml | 6.6 | 6.0 |
| | 10 µg/ml | 2.9 | 2.9 |
| Compound 30 | 2 µg/ml | 4.6 | 4.7 |

Test Example 2
[Effects on Delayed Neuronal Death of Gerbils after Cerebral Ischemia]

Effects on neuronal degeneration after cerebral ischemia were evaluated in models of bilateral common carotid occlusion of gerbils.
(Test Animals)
Male gerbils weighing 60 to 90 g (available from Shin-Nihon Dobutsu Co., Saitama, Japan) were used.
(Test Procedure)
The gerbils were slightly anesthetized with ether and fixed in the supine position. After local infiltration anesthesia with lidocaine, bilateral common carotid arteries were incised along the cervical median line, exposed and carefully dissected from the neighboring sympathetic nerves. The arteries were clamped with aneurysm clips for 3 minutes and then the clip was removed, followed by suturing the skins. Sham-operated animals were treated in the same manner as above except that no bilateral common carotid arteries were clamped. 7 days after the cerebral ischemia for 3 minutes, the animals were anesthetized with ether, and the brains were perfused with a 10% buffered formalin solution through the left cardiac ventricle.

Hippocampal regions were cut away as annular slices having a thickness of 3 to 4 mm, paraffin-embedded and then prepared into sections. Slices were stained with hematoxylin & eosin. Ischemic neuronal damage was classified into the following 4 stages, i.e. 0 to 3, for evaluation.

0(−): normal neurons

1(+): a few neurons damaged (as few as one neuron damaged)

2(++): many neurons damaged

3(+++): majority of neurons damaged (Test Samples)

Test samples were dissolved in saline solution and intraperitoneally administered at 10 mg/kg just after the end of ischemia.

(Results)

The hippocampal CA1 neurons were not damaged at all in the sham-operated gerbils whereas the hippocampal CA1 neurons appeared to be damaged by light microscopic examination in gerbils subjected to 3 minutes occlusion of bilateral common carotid arteries.

However, destruction and disappearance of hippocampal CA1 neurons were prevented by intraperitoneal administration of the present compounds. Results are shown in Table 4.

TABLE 4

| Test Samples | Dose (mg/kg, IP) | Test Runs | Incidence of neuronal changes (%) | | | |
|---|---|---|---|---|---|---|
| | | | − | + | ++ | +++ |
| Sham-operated group | — | 8 | 100 | 0 | 0 | 0 |
| 3-minute ischemia group | — | 8 | 0 | 0 | 0 | 100 |
| Compound 14 | 10 | 8 | 0 | 50 | 25 | 25 |

Test Example 3

[Effects on Cerebral Infarction Induced by Middle Cerebral Artery Occlusion in Stroke-prone Spontaneously Hypertensive Rats (SHRSP)]

[Test Samples]

Compound 14 and control test sample 1 [6,4'-(4-methylphenyl)-2,2':6',2''-terpyridine=trihydrochloride, a compound disclosed in WO94/14440] were used.

Structural formula of control test sample 1:

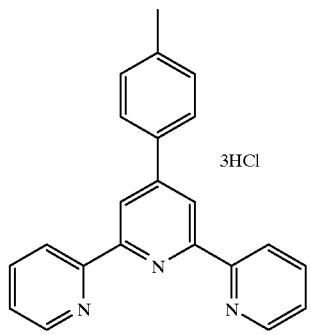

[Test Procedure]

Rats (SHRSP, ♂, 12–20 weeks) were anesthetized by halothane inhalation and body temperature was kept at about 37° C. The rats were fixed at the lateral position and the dura mater was incised. The left middle cerebral artery was occluded distal to the striate branches and 0.7–1 mm dorsal to the rhinal fissure, using a microbipolar coagulation. At the same times infusion pumps were set to the rats to conduct continual injection of test compounds from the tail veins at doses of 1 and 10 mg/kg/hr for 4 hours. The vehicle-treated group was used as control group. 7 days after the surgical operation, the brains were perfused with a 10% buffered formalin solution and then brains were dissected out to prepare serial sections. Brain sections were stained with hematoxylin & eosin, and then determined for areas as infarction by an image analyzer. Percentage of infarction per total brain area was calculated.

(Results)

As shown in FIG. 1, no effect in reducing the size of cerebral infarction was observed in control test sample 1, whereas Compound 14 reduced the size of infarction dose-dependently, compared with the control group.

Test Example 4

[Changes in Behavior after the Administration of Test Compounds]

(Test Procedure)

Control test sample 1 and Compound 14 were intravenously administered into rats of the same strain as used in Test Example 3 in doses of 10 and 40 mg/kg to observe behavior resulting therefrom.

(Results)

Control test sample 1 induced sedation at both dosages, whereas no behavioral changes were observed with Compound 14.

We claim:

1. A pyridine compound represented by the following formula (I):

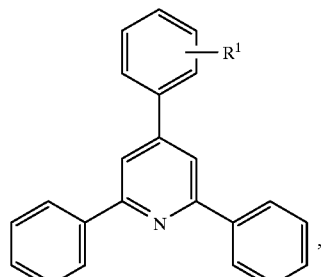

where $R^1$ is a functional group represented by any one of the following formulae (II)-1 to (II)-6:

(II)-1 —CONHCH$_2$CH$_2$N(CH$_3$)$_2$

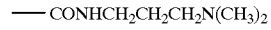
(II)-2 —CONHCH$_2$CH$_2$CH$_2$N(CH$_3$)$_2$

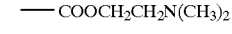
(II)-3 —COOCH$_2$CH$_2$N(CH$_3$)$_2$

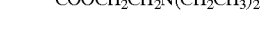
(II)-4 —COOCH$_2$CH$_2$N(CH$_2$CH$_3$)$_2$

(II)-5 —NHCOCH$_2$N(CH$_3$)$_2$

(II)-6 —NHCOCH$_2$N(CH$_2$CH$_3$)$_2$, or a salt thereof.

2. A pyridine compound represented by the following formula (III):

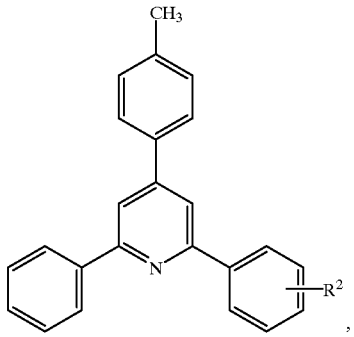

where $R^2$ is an amino group or a functional group represented by any one of the following formulae (IV)-1 to (IV)-5:

(IV)-1 —CONHCH$_2$CH$_2$N(CH$_3$)$_2$

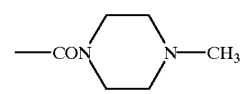
(IV)-2

-continued

—COOCH$_2$CH$_2$N(CH$_3$)$_2$ (IV)-3

—NHCOCH$_2$N(CH$_3$)$_2$ (IV)-4

—NHCOCH$_2$N(CH$_2$CH$_3$)$_2$, (IV)-5 or a salt thereof.

3. A pharmaceutical composition, which comprises an effective amount of a pyridine compound of claim 1 or a salt thereof.

4. A pharmaceutical composition, which comprises an effective amount of a pyridine compound of claim 2 or a salt thereof.

5. A pharmaceutical composition comprising a pyridine compound according to claim 1 for use in ameliorating or curing a neuronal degeneration disease.

6. A pharmaceutical composition comprising a pyridine compound according to claim 2 for use in ameliorating or curing a neuronal degeneration disease.

7. A method for ameliorating or curing a neuronal degeneration disease, which comprises administering an effective amount of a pyridine compound of claim 1 or a salt thereof to a human being.

8. A method for ameliorating or curing a neuronal degeneration disease, which comprises administering an effective amount of a pyridine compound of claim 2 or a salt thereof to a human being.

* * * * *